United States Patent
Woeller et al.

(10) Patent No.: US 9,801,971 B2
(45) Date of Patent: Oct. 31, 2017

(54) TRANSDERMAL THERAPEUTIC PATCHES CONTAINING 4-N-BUTYLRESORCINOL

(75) Inventors: Karl-Heinz Woeller, Hamburg (DE); Ludger Kolbe, Dohren (DE); Cathrin Scherner, Norderstedt (DE); Rainer Wolber, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 13/499,861

(22) PCT Filed: Jul. 14, 2010

(86) PCT No.: PCT/EP2010/004272
§ 371 (c)(1),
(2), (4) Date: Jun. 25, 2012

(87) PCT Pub. No.: WO2011/042077
PCT Pub. Date: Apr. 14, 2011

(65) Prior Publication Data
US 2012/0259020 A1    Oct. 11, 2012

(30) Foreign Application Priority Data
Oct. 9, 2009 (DE) .......................... 10 2009 048 973

(51) Int. Cl.
*A61K 31/05* (2006.01)
*A61L 15/44* (2006.01)
*A61K 9/70* (2006.01)

(52) U.S. Cl.
CPC ............ *A61L 15/44* (2013.01); *A61K 9/7053* (2013.01); *A61K 9/7061* (2013.01); *A61K 9/7076* (2013.01); *A61L 2300/216* (2013.01); *A61L 2300/404* (2013.01)

(58) Field of Classification Search
CPC  A61Q 19/00; A61Q 1/02; A61L 15/44; A61L 2300/216; A61K 9/7076; A61K 9/7053
USPC .............................. 514/731; 568/766; 424/62
See application file for complete search history.

(56) References Cited

U.S. PATENT DOCUMENTS

| | | | |
|---|---|---|---|
| 4,393,150 A * | 7/1983 | Kresner ......................... | 523/111 |
| 4,588,580 A * | 5/1986 | Gale et al. ..................... | 424/449 |
| 4,959,393 A * | 9/1990 | Torihara et al. ............... | 514/724 |
| 5,508,038 A * | 4/1996 | Wang et al. ................... | 424/448 |
| 5,891,463 A | 4/1999 | Bello et al. | |
| 6,072,100 A * | 6/2000 | Mooney et al. ................ | 602/48 |
| 6,830,758 B2 | 12/2004 | Nichols et al. | |
| 6,869,598 B2 | 3/2005 | Love et al. | |
| 7,829,099 B2 * | 11/2010 | Woeller et al. .......... | 424/195.17 |
| 2003/0175333 A1 | 9/2003 | Shefer et al. | |
| 2003/0185773 A1 | 10/2003 | Love et al. | |
| 2004/0009202 A1 | 1/2004 | Woller | |
| 2005/0281869 A1 | 12/2005 | Kruse et al. | |
| 2007/0122367 A1 * | 5/2007 | Bradley et al. ................ | 424/62 |
| 2011/0274727 A1 | 11/2011 | Andres et al. | |
| 2011/0305654 A1 | 12/2011 | Mallard et al. | |

FOREIGN PATENT DOCUMENTS

| | | |
|---|---|---|
| DE | 10260872 | 7/2004 |
| EP | 0341664 A1 | 11/1989 |
| JP | 11-228340 A * | 8/1999 |
| WO | 0238196 A2 | 5/2002 |
| WO | 03800009 A1 | 10/2003 |
| WO | 2004078122 A2 | 9/2004 |
| WO | 2009156676 A1 | 12/2009 |
| WO | 2010049462 A1 | 5/2010 |

OTHER PUBLICATIONS

Panigrahi et al.; Title: The effect of pH and organic ester penetration enhancers on skin permeation kinetics of terbutaline sulfate from pseudolatex-type transdermal delivery systems through mouse and human cadaver skins; AAPS PharmSciTech., vol. 6(2): pp. E167-E173, Published online Sep. 30, 2005.*
Chemical properties, data retrived from American Chemical Socient via SciFinder on 04/06/201.*
Novel Dosage Form and Technology of Drugs, by Lu Bin, People's Medical Publishing House, second edition, Jul. 2005, pp. 568-570.

* cited by examiner

*Primary Examiner* — Yanzhi Zhang
(74) *Attorney, Agent, or Firm* — Abel Law Group, LLP

(57) ABSTRACT

Transdermal therapeutic systems that contain 4-n-butylresorcinol as an active ingredient.

19 Claims, No Drawings

TRANSDERMAL THERAPEUTIC PATCHES CONTAINING 4-N-BUTYLRESORCINOL

BACKGROUND OF THE INVENTION

1. Field of the Invention

The present invention relates to transdermal therapeutic systems, self-adhesive flat bandages, in particular cosmetic and medicinal plasters, containing 4-n-butylresorcinol.

2. Discussion of Background Information

Melanocytes are responsible for the pigmenting of the skin; these are found in the lowest layer of the epidermis, the Stratum basale, alongside the basal cells as pigment-forming cells which, depending on the skin type, occur either individually or in clusters of varying size.

Melanocytes contain, as characteristic cell organelles, melanosomes, in which the melanin is formed. Inter alia, upon stimulation by UV radiation, melanin is formed to a greater extent. It is transported via the living layers of the epidermis (keratinocytes) ultimately into the horny layer (corneocytes) and brings about a more or less pronounced brownish to brown-black skin color.

Melanin is formed as the end stage of an oxidative process in which tyrosine is converted, under the co-action of the enzyme tyrosinase, via several intermediates, to the brown to brown-black eumelanins (DHICA and DHI melanin), or, with the participation of sulfur-containing compounds, to the reddish pheomelanin. DHICA and DHI melanin are formed via the common intermediates dopaquinone and dopachrome. The latter, sometimes with the participation of further enzymes, is converted either to indole-5,6-quinonecarboxylic acid or into indole-5,6-quinone, from which the two specified eumelanins are formed.

The formation of pheomelanin proceeds inter alia via the intermediates dopaquinone and cysteinyldopa. The expression of the melanin-synthesizing enzymes is controlled by a specific transcription factor (microphthalmia-associated transcription factor, MITF). Besides the described enzymatic processes of the melanin synthesis, further proteins are also of importance for the melanogenesis in the melanosomes. An important role here appears to be attributed to the so-called p-protein, although the exact function is still unclear.

As well as the above-described process of the melanin synthesis in the melanocytes, the transfer of the melanosomes, their stay in the epidermis and also their degradation and the degradation of the melanin are also of decisive importance for the pigmenting of the skin. It was shown that the PAR-2 receptor is important for the transport of the melanosomes from the melanocytes into the keratinocytes (M. Seiberg et al., 2000, J. Cell. Sci., 113:3093-101).

In addition, the size and shape of the melanosomes have an influence on their light-scattering properties and thus the color appearance of the skin. For example, in black Africans there are more large spheroidal individual melanosomes whereas in Caucasians, smaller melanosomes occurring in groups are to be found.

Problems with hyperpigmentation of the skin have a wide variety of causes and/or are accompanying phenomena of many biological processes, e.g. UV radiation (e.g. freckles, Ephelides), genetic disposition, incorrect pigmentation of the skin during wound healing or scarring (post-inflammatory hyperpigmentation) or skin aging (e.g. Lentigines seniles).

After inflammatory reactions, the pigmentation system of the skin reacts with sometimes opposite reactions. This can lead either to post-inflammatory hyperpigmentations or hypopigmentations. Post-inflammatory hypomelanoses often arise inter alia in conjunction with atopy, Lupus erythematosus and psoriasis. The different reaction forms of the pigmentation system of human skin as a result of inflammatory phenomena are understood only very incompletely.

Problems with post-inflammatory hyperpigmentation often occur in darker skin types. Particularly in colored males, the problem of Pseudofollikulitis barbae is known, which is associated with cosmetically undesired incorrect pigmentation and/or leads to this. Forms of melasma, which occur in particular in women of Asiatic origin on the face and on the décolletage area, and also various forms of irregular pigmentation of the skin are also types of post-inflammatory hyperpigmentations. In addition, dark circles around the eyes are also considered to be a form of post-inflammatory hyperpigmentations, the underlying inflammation in most cases proceeding without clinical manifestations.

In many cases, post-inflammatory incorrect pigmentation of this type is increased further by the action of sunlight (UV light) without resulting in a UV-induced inflammation (sunburn).

Active ingredients and preparations are known which counteract skin pigmentation. In practical use are essentially preparations based on hydroquinone, although, on the one hand, these only exhibit their effect after application for several weeks, and, on the other hand, their excessively long application is unacceptable for toxicological reasons. Albert Kligman et al. has developed a so-called triformula which constitutes a combination of 0.1% tretinoin, 5.0% hydroquinone, 0.1% dexamethasone (A. Kligman, 1975, Arch. Dermatol., 111:40-48). However, this formulation too is highly disputed on account of possible irreversible changes in the pigmentation system of the skin.

In addition, skin-peeling methods (chemical and mechanical peels) are used, although these often lead to inflammatory reactions and, on account of post-inflammatory hyperpigmentations which may subsequently arise, can even lead to greater pigmentation instead of reduced pigmentation. All of these customary methods, which are also used for treating post-inflammatory hyperpigmentations, are characterized by distinct side effects.

Cosmetic preparations with 4-n-butylresorcinol are known, for example from EP 1 490 017.

4-n-Butylresorcinol, CAS[18979-61-8], is characterized by the chemical structure

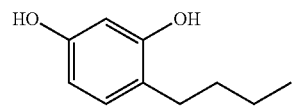

4-n-Butylresorcinol is also called rucinol or lucinol. It inhibits the production of melanin by inhibiting the enzyme tyrosinase required for the synthesis of melanin (melanogenesis). The production of melanin is firstly inhibited, then the production of black melanin, which is responsible for the intense coloration of pigment spots, is blocked.

4-n-Butylresorcinol has the formulatory disadvantage that it has a tendency to discolor—and to discolor cosmetic or dermatological preparations comprising it.

Transdermal therapeutic systems ("TTS") are known per se. A disadvantage of TTS is that usually only ca. 10% to 20% of the active ingredient content of the plaster are released during the application time. (Kommentar zum Europäischen Arzneibuch [Commentary on the European pharmacopeia], Wissenschaftliche Verlagsgesellschaft Stuttgart, status: update 2009).

It was therefore the object of the invention below to provide remedies for the disadvantages of the prior art.

SUMMARY OF THE INVENTION

The present invention provides a transdermal therapeutic system, which system comprises 4-n-butylresorcinol as an active ingredient.

In one aspect, the system may be present as a self-adhesive flat bandage, e.g., as a cosmetic plaster and/or a medicinal plaster.

In another aspect, the system may be present in the form of a matrix system. For example, the matrix may be selected from nonpolar matrices based on synthetic and natural rubber, polar wet adhesive films based on polyacrylic acid/polyvinyl alcohol, nonpolar matrices based on polyacrylic acid copolymers, polar anhydrous gel matrices based on polyacrylic acid/polyvinylpyrrolidone, nonpolar polyisobutylene matrices, and polar water gel matrices based on agar agar/polyacrylic acid.

In yet another aspect, the system of the present invention may comprise from 0.001% to 10%, e.g., from 0.01% to 1% by weight of 4-n-butylresorcinol, based on the total weight of the system.

In a still further aspect, the system may comprise one or more penetration accelerators such as, e.g., isopropyl palmitate and/or isopropyl myristate. For example, the one or more penetration accelerators may be present at a concentration of from 0.001% to 10%, e.g., from 0.01% to 7.5% or from 0.1% to 5% by weight.

In another aspect, the system may release 4-n-butylresorcinol at a rate of >30%/24 h, e.g., at a rate of 55-65%/24 h.

The present invention also provides a transdermal therapeutic system that comprises from 0.01% to 1% by weight of 4-n-butylresorcinol and from 0.1% to 5% by weight of one or more penetration accelerators which comprise isopropyl palmitate and/or isopropyl myristate.

In one aspect, the system may be present in the form of a matrix system, and the matrix may be selected from polar water gel matrices based on agar agar/polyacrylic acid and nonpolar polyisobutylene matrices.

In another aspect, the system may release 4-n-butylresorcinol at a rate of >30%/24 h.

The present invention also provides a method for the treatment of a local pigmentation disorder. The method comprises the application of the transdermal therapeutic system of the present invention set forth above (including the various aspects thereof) onto skin affected by the disorder.

In one aspect of the method, the disorder may comprise local hyperpigmentation such as, e.g., one or more of age spots, freckles, post-inflammatory hyperpigmentation (e.g. as a result of Pseudofollikulitis barbae), and melasma.

DETAILED DESCRIPTION OF THE INVENTION

It was surprising and unforeseeable for the person skilled in the art that shortcomings in the prior art are overcome by transdermal therapeutic systems which contain 4-n-butylresorcinol as active ingredient.

To produce an effective self-adhesive plaster comprising 4-butylresorcinol with optimized release for the treatment of pigment disorders of the skin, various self-adhesive matrix systems with 1% of the active ingredient were produced and investigated with regard to their release properties after 24 hours on pig skin by means of Franz cells:

A nonpolar matrix based on synthetic and natural rubber (KA)

A polar wet adhesive film based on polyacrylic acid/polyvinyl alcohol (FKF)

A nonpolar matrix based on a polyacrylic acid copolymer (PAC)

A polar anhydrous gel matrix based on polyacrylic acid/polyvinylpyrrolidone (WFG)

A nonpolar polyisobutylene matrix (PIB)

A polar water gel matrix based on agar agar/polyacrylic acid (WG)

Results of the active ingredient release of different matrix systems:

| (KA) | (FKF) | (PAC) | (WFG) | (PIB) | (WG) |
| --- | --- | --- | --- | --- | --- |
| 7.4% | 17.8% | 18.1% | 20.6% | 22.2% | 34.0% |

Based on the above first results, the nonpolar polyisobutylene matrix and the polar water gel matrix were selected for further optimization experiments with regard to the release of 4-n-butylresorcinol.

The active ingredient release can advantageously be controlled by virtue of the layer thickness of the TTS.

For both systems, PIB and WG, in each case samples with a layer thickness of 1.00; 0.75; 0.50; 0.30 and 0.15 mm were produced and investigated.

Results of the active ingredient release of different matrix layer thicknesses:

|  | 1.00 mm | 0.75 mm | 0.50 mm | 0.30 mm | 0.15 mm |
| --- | --- | --- | --- | --- | --- |
| (PIB) | 22.2% | 27.4% | 26.7% | 42.7% | 46.4% |
| (WG) | 34.0% | 48.3% | 41.8% | 66.2% | 56.8% |

As a compromise between percentage active ingredient release, absolute released amount of active ingredient and handlability of the finished self-adhesive plaster, for both matrix systems, a layer thickness between 1.00 mm and 0.01 mm, preferably 0.50 and 0.20 mm and very particularly preferably of 0.30 mm is considered. In particular, the self-adhesive patch based on a polar water gel according to the invention exhibits, with around 65% of the active ingredient, a surprisingly high release compared to customary plaster applications.

In order to likewise bring the PIB matrix system into this active ingredient release range, further experiments were carried out by means of incorporating customary additives for increasing the hydrophilicity of the matrix, and also customary penetration accelerators.

The incorporation of 35% cellulose into the PIB matrix revealed no significant difference in the active ingredient release compared with a matrix not filled with cellulose.

As customary penetration accelerators, in each case 5% isopropyl palmitate (IPP) and 5% isopropyl myristate (IPM) were then incorporated into a corresponding PIB matrix, and the release of 4-n-butylresorcinol from the end products produced therefrom of layer thickness 0.30 mm was determined.

Results of the PIB matrix active ingredient release of different penetration accelerators:

|  | PIB matrix plus 5% IPP | PIB matrix plus 5% IPM |
|---|---|---|
| Release of 4-n-butyl-resorcinol | 33.2% | 61.3% |

Surprisingly, the addition of 5% IPM exhibited almost twice as high an active ingredient release from the PIB matrix as the addition of the homologous penetration accelerator IPP.

With around 61% release of 4-n-butylresorcinol from the nonpolar PIB matrix, it was possible to achieve an analogous order of magnitude as from the polar water gel matrix with around 65%.

Examples of the preparation of polar self-adhesive water gel matrices are described in DE 102 60 872.

Examples of the preparation of nonpolar self-adhesive PIB matrices are described in EP 1335755.

Suitable carrier materials for polar and nonpolar self-adhesive patches according to the invention with optimized active ingredient release for the treatment of pigment disorders of the skin are all customary flat layered materials such as, for example, woven fabrics, films, nonwoven fabrics etc. In the case of the last-mentioned carrier materials, in particular so-called non-wovens of small layer thickness are advantageous because these are barely noticeable in visual terms on the matrices against the skin. The use of very thin, layer thickness below 100 μm, flexible and transparent to translucent polymer films, in particular those polyurethane films produced from aqueous dispersion, is particularly advantageous.

However, it is also possible to use films from all other known polymer films, such as e.g. polyethylene, ethylvinylacetate etc. In the case of the polyisobutylene matrix, when using carrier materials with significantly different water vapor transmission rates (WVTR) of 5933.5 g/m$^2$*24 h (viscose) via 1509.9 g/m$^2$*24 h (polyurethane) to 25.7 g/m$^2$*24 h (polyethylene), no significant differences could be established in the active ingredient release. The reason for this is the hydrophobicity of the PIB matrix as determining factor for the WVTR. When using hydrophilic fillers, such as e.g. cellulose or polyacrylic acid derivatives, in a PIB matrix, however, carrier materials of different WVTR can become relevant again as the determining factor of the active ingredient release.

In the case of the water gel, the active ingredient release can be significantly influenced by the WVTR of the carrier material used. Thus, e.g. samples with viscose carrier exhibited a 14% higher active ingredient release compared with samples with PU carriers.

Since the water gel matrices and also polyisobutylene matrices according to the invention are transparent to at most translucent, patches laminated with the above-described films as carrier materials are barely noticeable in visual terms and can therefore also be used inconspicuously over prolonged periods. As a result of appropriate coloring of the matrices or covering with a precolored carrier, a patch according to the invention, however, can also be produced in an inconspicuous skin shade.

Self-adhesive patches according to the invention can have any desired shape and size, e.g. round, rectangular, square etc. It is particularly advantageous that patches according to the invention based on PIB and on WG can be rightly cut by the user into any desired shape and size using standard commercial scissors in order to tailor the patch exactly to the desired treatment area.

It has been found that the water gel matrices and polyisobutylene matrices according to the invention have proven to be particularly easy to handle and effective particularly for the treatment of local hyperpigmentations such as age spots, freckles, post-inflammatory hyperpigmentations (e.g. as a consequence of Pseudofollikulitis barbae) if they are present in round to oval form with a diameter of ≤20 mm, preferably ≤15 mm, very particularly preferably ≤10 mm.

It has been found that the water gel matrices and also polyisobutylene matrices according to the invention have proven to be particularly easy to handle and effective particularly for the treatment of local hyperpigmentations such as melasma if they have an area ≥25 cm$^2$, preferably ≥15 cm$^2$, very particularly preferably ≥4 cm$^2$.

EXAMPLES

Example 1; Wet Adhesive Film Based on Polyacrylic Acid/Polyvinyl Alcohol (FKF)

|  | % by weight |
|---|---|
| Polyvinyl alcohol | 68.0 |
| Polyacrylic acid | 16.5 |
| Polyethylene glycol 400 | 9.5 |
| Glycerol | 5.0 |
| 4-n-Butylresorcinol | 1.0 |

Example 2; Polar Anhydrous Gel Matrix, Polyacrylic Acid/Polyvinylpyrrolidone Base (WFG)

|  | % by weight |
|---|---|
| Dexpanthenol | 3.0 |
| Propanediol | 5.0 |
| Polyethylene glycol 400 | 18.0 |
| Polyacrylic acid | 22.5 |
| Polyvinylpyrrolidone | 3.5 |
| Silicon dioxide | 4.0 |
| Glycerol | 43.0 |
| 4-n-Butylresorcinol | 1.0 |

Example 3; Nonpolar Polyisobutylene Matrix (PIB)

|  | % by weight |
|---|---|
| PIB 12 | 21.5 |
| PIB 80 | 20.0 |
| PIB 12 | 10.0 |
| Cellulose | 33.0 |
| Isopropyl myristate | 5.0 |
| Decyl oleate | 9.5 |
| 4-n-Butylresorcinol | 1.0 |

Example 4; Polar Water Gel Matrix Based on Agar Agar/Polyacrylic Acid (WG)

|  | % by weight |
| --- | --- |
| Water | 49.1 |
| Sorbitol | 15.7 |
| Agar agar | 2.0 |
| Glycerol | 20.0 |
| Polyacrylic acid | 8.0 |
| NaOH 45% | 4.2 |
| 4-n-Butylresorcinol | 1.0 |

What is claimed is:

1. A transdermal therapeutic patch, wherein the patch consists of a self-adhesive transdermal matrix system having a layer thickness of from 0.15 mm to 0.75 mm on a carrier material selected from woven fabrics, non-woven fabrics and polymer films, and wherein the matrix system comprises, as the only matrix, a matrix selected from nonpolar polyisobutylene matrices, the said matrix contains 4-n-butylresorcinol as therapeutic ingredient in a concentration of from 1% to 10% by weight, based on a total weight of the matrix system.

2. The transdermal therapeutic patch of claim 1, wherein the matrix system has a layer thickness of from 0.15 mm to 0.50 mm.

3. The transdermal therapeutic patch of claim 1, wherein the matrix system has a layer thickness of from 0.15 mm to 0.30 mm.

4. The transdermal therapeutic patch of claim 1, wherein the matrix system further comprises from 5% to 10% by weight of one or more penetration accelerators, based on a total weight of the matrix system.

5. The transdermal therapeutic patch of claim 4, wherein the one or more penetration accelerators comprise isopropyl myristate.

6. The transdermal therapeutic patch of claim 1, wherein the carrier material is selected from non-woven fabrics.

7. The transdermal therapeutic patch of claim 1, wherein the carrier material is selected from polymer films.

8. The transdermal therapeutic system of claim 7, wherein the carrier material is a transparent to translucent polymer film having a thickness of below 100 µm.

9. The transdermal therapeutic system of claim 7, wherein the polymer film is a polyurethane film.

10. A transdermal therapeutic patch, wherein the patch consists of a self-adhesive transdermal matrix system having a layer thickness of from 0.15 mm to 1.00 mm on a carrier material selected from woven fabrics, non-woven fabrics and polymer films, and wherein the matrix system comprises, as the only matrix, a matrix selected from polar agar agar/polyacrylic acid water gel matrices, the said matrix contains 4-n-butylresorcinol as therapeutic ingredient in a concentration of from 1% to 10% by weight, based on a total weight of the matrix system.

11. The transdermal therapeutic patch of claim 10, wherein the matrix system has a layer thickness of from 0.15 mm to 0.50 mm.

12. The transdermal therapeutic patch of claim 10, wherein the matrix system has a layer thickness of 0.30 mm.

13. The transdermal therapeutic patch of claim 10, wherein the carrier material is selected from non-woven fabrics.

14. The transdermal therapeutic patch of claim 10, wherein the carrier material is selected from polymer films.

15. The transdermal therapeutic system of claim 14, wherein the carrier material is a transparent to translucent polymer film having a thickness of below 100 µm.

16. The transdermal therapeutic system of claim 14, wherein the polymer film is a polyurethane film.

17. The transdermal therapeutic patch of claim 10, wherein the matrix system further contains from 5% to 10% by weight of one or more penetration accelerators, based on a total weight of the matrix system.

18. The transdermal therapeutic patch of claim 17, wherein the one or more penetration accelerators comprise at least one of isopropyl myristate and isopropyl palmitate.

19. The transdermal therapeutic patch of claim 4, wherein the one or more penetration accelerators comprise isopropyl palmitate.

\* \* \* \* \*